US008252356B2

(12) United States Patent
Ogura et al.

(10) Patent No.: US 8,252,356 B2
(45) Date of Patent: Aug. 28, 2012

(54) FLAVOR COMPOSITION OR FRAGRANCE COMPOSITION

(75) Inventors: Miharu Ogura, Kanagawa (JP);
Yoshihiro Yaguchi, Kanagawa (JP);
Makoto Emura, Kanagawa (JP);
Toshihiro Takeda, Kanagawa (JP);
Yoshifumi Yuasa, Kanagawa (JP);
Shigeyuki Sasaki, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 13/064,389

(22) Filed: Mar. 22, 2011

(65) Prior Publication Data

US 2011/0171358 A1    Jul. 14, 2011

Related U.S. Application Data

(62) Division of application No. 11/991,806, filed as application No. PCT/JP2006/317822 on Sep. 8, 2006.

(30) Foreign Application Priority Data

Sep. 12, 2005   (JP) .................................. 2005-263950
Sep. 12, 2005   (JP) .................................. 2005-263951

(51) Int. Cl.
*A23L 1/22*   (2006.01)
*A23L 2/56*   (2006.01)
(52) U.S. Cl. ........................................................ 426/535
(58) Field of Classification Search .................. 426/533, 426/535, 650
See application file for complete search history.

(56) References Cited

U.S. PATENT DOCUMENTS

| | | | | |
|---|---|---|---|---|
| 3,879,562 A | 4/1975 | Pittet et al. | ..................... | 426/535 |
| 4,271,853 A | 6/1981 | Mookherjee et al. | ......... | 131/276 |
| 4,667,223 A | 5/1987 | Flamm | ........................... | 560/147 |
| 5,496,580 A * | 3/1996 | Amano et al. | ................. | 426/534 |

OTHER PUBLICATIONS

Cuer, A. et al., "Flavour Properties of some Sulphur Compounds Isolated from Cheeses", *Lebensmittel-Wissenschaft und Technologie*, 1979, 12(5), pp. 258-261.
Shuchi•Kan'yo Gijutsushu (Koryo), Dai I Bu Koryo Ippan, Japanese Patent Office, 1999, p. 2.
Vasi, I.G. et al., "Synthesis of Optically Active Thiolesters From S-(+)-1-Methylbutyric Acid", *Journal of the Institution of Chemists* (India), 1973, 45(2), pp. 51-54.
Laurence GIJS et al, "Retention of sulfur flavours by food matrix and determination of sensorial data independent of the medium composition" Food Chemistry 69, pp. 319-330 (2000).
J. Haley et al, "Differences in Utilisation of the Essential Oil of Hops During the Production of Dry-Hopped and Late-Hopped Beers" J. Inst. Brew, vol. 89(2) pp. 87-91 (1983).
J.C. Seaton et al, "High temperature wort boiling—consequence for beer flavour" Proceedings of Congress—European Brewery Convention (EBC Congress), 18th, pp. 161-168 (1981).

A. Sugget et al, "The Role of Sulphur Compounds in Hop Flavor" EBC Congress 17th, pp. 79-89 (1979).
T.L Peppard et al, "Hop Derived Sulphur Compounds and Their Effect on Beer Flavor" EBC Congress 17th, pp. 91-104 (1981).
James C. Seaton et al, "The Flavor Contribution of Sulfur Compounds in Hops" 2nd MBAA Symposium on Sensory Analysis 18(1), pp. 26-30 (1981).
G. Dauphin et al, "RMN du $^{13}$C de Composés Méthylés Soufrés" Organic Magnetic Resonance 12(10), pp. 557-560 (1979).
J.A. Picket, "Studies on Flavour-active Sulphur Components of Hops and Beer" Proceedings of the Analytical Division of the Chemical Society, 13(7), pp. 215-217 (1976).
John Idoux et al, "Study of the Alkaline Hydrolysis and Nuclear Magnetic Resonance Spectra of Some Thiol Eaters" Journal of Organic Chemistry 38(24), pp. 4239-4443 (1973).
R. Näf et al, "Sulphur Compounds and Some Uncommon Esters in Durian" Flavour and Fragrance Journal, 11 (5), pp. 295-303(1996).
J.W.K. Burrell et al, "Characterisation of Thiol Esters in Galbanum Oil." Tetrahedron Letters No. 30, pp. 2837-2838 (1971).
B. A. McAndrew, et al."Analysis of Galbanum Oils" Developments in Food Science, 18 (Flavors Fragrances), pp. 573-585 (1988).
Abstracts book of 32nd Symposium on the Chemistry of Terpenes, Essential Oils, and Aromatics, pp. 31-33 (1988).
Shinohara Asao, et al. "Studies on a scent component of a melon fruit (first report) Monitoring of the ripeness and the change in scent of a muskmelon based on head space analysis", The 32nd Symposium on the Chemistry of Terpenes, Essential Oils, and Scenttics, Oct. 24-26, 1988.
Ogura et al. "Chiraroma Analysis (1) Characteristic Aroma Components of Melon" , Nov. 2005, Proceeding Symposium on Chemistry and Essential Oil Fragrance, 49, Abstract.
The Good Scents Company, "S-methyl 2-methyul butane thioate", Jun. 2006, retrived from the Internet: URL: http://web.archive.org/web/20060605033510/http://www.thegoodscentscompany.com/data/rw1131201.html.
Kourkoutas et al., "Comparison of the Volatile Compositions and Flavor Properties of Cantaloupe, Galia, and Honeydew Muslmelons", May 2005, retrived from the Internet doi: 10.1016/j.physletb.2003. 10071.
English translation of Ogura, "Chiraroma Analysis (1) Characteristic Aroma Components of Melon".
Rowe et al., "More Fizz for Your Buck: High-Impact Aroma Chemicals", Sep./Oct. 2000, Perfumer & Flavorist Magazine, vol. 25, No. 5, pp. 1-19.

* cited by examiner

*Primary Examiner* — Humera Sheikh
*Assistant Examiner* — Tynesha McClain-Coleman
(74) *Attorney, Agent, or Firm* — Kubovcik & Kubovcik

(57) ABSTRACT

The present invention relates to a flavor composition or fragrance composition which can satisfy diversified requirements for flavored products, as well as to a flavor-improving agent which can improve the quality and release of aroma of a beverage or food. More particularly, the present invention relates to a flavor composition or fragrance composition which comprises an optically active S-alkyl 2-methylbutanethioate as an active ingredient, a flavor- or fragrance-added product, a flavor-improving agent which comprises an optically active S-alkyl 2-methylbutanethioate as an active ingredient, and a beverage or food having an improved flavor. The optically active S-alkyl 2-methylbutanethioate includes S-alkyl(R)-2-methylbutanethioate and S-alkyl(S)-2-methylbutanethioate.

9 Claims, No Drawings

FLAVOR COMPOSITION OR FRAGRANCE COMPOSITION

This application is a division of application Ser. No. 11/991,806, filed Mar. 26, 2008, which is a 371 of international application PCT/JP2006/317822, filed Sep. 8, 2006, which claims priority based on Japanese Patent Application Nos. 2005-263950 and 2005-263951, each filed Sep. 12, 2005, and which are incorporated herein by reference.

TECHNICAL FIELD

The present invention relates to a flavor composition or fragrance composition which can satisfy diversified requirements for flavored products, as well as to a flavor-improving agent which can improve the quality and release of odor of a beverage or food. More particularly, the present invention relates to a flavor composition or fragrance composition which comprises an optically active S-alkyl 2-methylbutanethioate as an active ingredient, a flavor- or fragrance-added product, a flavor-improving agent which comprises an optically active S-alkyl 2-methylbutanethioate as an active ingredient, and a beverage or food having an improved flavor.

BACKGROUND ART

Many of the compounds which have been used as a flavor component, a fragrance component or a flavor-improving agent in beverages, foods, cosmetics, etc., are racemic forms. For example, S-alkyl 2-methylbutanethioates are known to be present as racemic forms in natural products, particularly in fruits and beer (non-patent literatures 1 to 13). Of these racemic S-alkyl 2-methylbutanethioates, S-methyl 2-methylbutanethioate, in particular, is in use for the purpose of providing, for example, an odor of food fermentation or a feeling of ripe fruit.

The flavor component or fragrance component comprising such a racemic S-alkyl 2-methylbutanethioate as an active ingredient is satisfactory to some extent in that it provides a good fermentation odor or a feeling of ripe fruit; however, it is not sufficient. Also, the flavor-improving agent comprising the racemic S-alkyl 2-methylbutanethioate as an active ingredient, still has much room for improvement in release of odor.

Meanwhile, in connection with the analysis of the odorous component of cheese, there was made a chromatographic analysis on S-methyl(S)-2-methylbutanethioate and racemic S-methyl 2-methylbutanethioate, and their odor characteristics were reported (non-patent literature 14). Also, in connection with the analysis of the odorous component of hop, the odor characteristic of racemic S-methyl 2-methylbutanethioate was reported. (non-patent literature 8).

According to the descriptions in these literatures, the odor characteristic of racemic S-methyl 2-methylbutanethioate is wild strawberry (non-patent literature 14), or cooked vegetable, sulphury or soapy/fatty (non-patent literature 8), and the odor characteristic of S-methyl(S)-2-methylbutanethioate is rubbery (non-patent literature 14).

However, none of these reports mentions the odor of S-alkyl(R)-2-methylbutanethioate, such as S-methyl(R)-2-methylbutanethioate. Further, each of these reports evaluated only the odor characteristics of single compounds, having no direct connection with the flavors of beverages or foods, and made no evaluation on the flavors and odor releases when S-alkyl(S)-2-methylbutanethioate had been actually used in beverages or foods (although, in these reports, there are descriptions on S-alkyl(S)-2-methylbutanethioate).

Non-patent literature 1: Food Chemistry (2000), 69 (3), 319-330
Non-patent literature 2: Journal of the Institute of Brewing (1983), 89 (2), 87-91
Non-patent literature 3: Proceedings of the Congress-European Brewery Convention (1981), 18th, 161-8
Non-patent literature 4: Proceedings of the Congress-European Brewery Convention (1979), 17th, 79-89
Non-patent literature 5: Proceedings of the Congress-European Brewery Convention (1981), 17th, 91-104
Non-patent literature 6: Technical Quarterly-Master Brewers Association of the Americas (1981), 18(1), 26-30
Non-patent literature 7: Organic Magnetic Resonance (1979), 12(10), 557-60
Non-patent literature 8: Proceedings of the Analytical Division of the Chemical Society (1976), 13(7), 215-17
Non-patent literature 9: Journal of Organic Chemistry (1973), 38 (24), 4239-43
Non-patent literature 10: Flavour and Fragrance Journal (1996), 11 (5), 295-303
Non-patent literature 11: Tetrahedron Letters (1971), (30), 2837-8
Non-patent literature 12: Development in Food Science (1988), 18 (Flavors Fragrances), 573-85
Non-patent literature 13: Abstrack book of $32^{nd}$ Symposium on the Chemistry of Terpenes, Essential oils, Aromatics, 31 to 33 pages, Oct. 24, 1988.
Non-patent literature 14: Lebensmittel-Wissenschaft und—Technologie (1979), 12 (5), 258-61

DISCLOSURE OF THE INVENTION

Task to be Achieved by the Invention

The present invention has been made under the background of the above-mentioned prior art and aims at providing a highly-taste, superior flavor composition or fragrance composition which can satisfy diversified requirements for flavored products, and a flavor-improving agent which can improve the quality and release of the odor of beverage or food.

Means for Achieving the Task

The present invention has achieved the above task by the following (1) to (18).

(1) A flavor composition or fragrance composition and a flavor-improving agent, characterized by comprising an optically active S-alkyl 2-methylbutanethioate as an active ingredient.
(2) A flavor composition or fragrance composition characterized by comprising an S-alkyl(R)-2-methylbutanethioate as an active ingredient.
(3) A flavor composition or fragrance composition according to (2), wherein the S-alkyl(R)-2-methylbutanethioate has an optical purity of 50% e.e. or more.
(4) A flavor composition or fragrance composition according to any of (1) to (3), which is a flavor composition.
(5) A flavor composition characterized by comprising an S-alkyl(R)-2-methylbutanethioate at a concentration of $10^{-6}$ to $10^7$ ppb.
(6) A product added with a flavor by a flavor composition set forth in (5).
(7) A flavor-added product according to (6), which is one member selected from beverages, foods, oral-care compositions and medicines.

(8) A product added with a flavor, characterized by being obtained by adding an S-alkyl(R)-2-methylbutanethioate at a concentration of $10^{-9}$ to $10^5$ ppb.
(9) A flavor composition or fragrance composition according to any of (1) to (3), which is a fragrance composition.
(10) A fragrance composition characterized by comprising an S-alkyl(R)-2-methylbutanethioate at a concentration of $10^{-6}$ to $10^7$ ppb.
(11) A product added with a fragrance by a fragrance composition set forth in (10).
(12) A fragrance-added product according to (11), which is one member selected from fragrance products, skin-care preparations, make-up cosmetics, hair cosmetics, sunblock cosmetics, medicated cosmetics, hair-care products, soaps, body cleaners, bath preparations, detergents, fabric softeners, cleaning agents, kitchen cleaners, bleaching agents, aerosols, deodorant-aromatics, repellants and sundries.
(13) A product added with a fragrance, characterized by being obtained by adding an S-alkyl(R)-2-methylbutanethioate at a concentration of $10^{-9}$ to $10^7$ ppb.
(14) A method for intensification, improvement or modification of flavor or fragrance, characterized by adding an S-alkyl(R)-2-methylbutanethioate.
(15) A flavor-improving agent characterized by comprising, as an active ingredient, an S-alkyl(S)-2-methylbutanethioate having an optical purity of 70% e.e. or more.
(16) A flavor-improving agent according to (15), wherein the S-alkyl(S)-2-methylbutanethioate is S-methyl(S)-2-methylbutanethioate.
(17) A beverage or food having an improved flavor, characterized by comprising an S-alkyl(S)-2-methylbutanethioate having an optical purity of 70% e.e. or more, at a proportion of $10^{-8}$ to $10^5$ ppb when converted to 100% optical purity.
(18) A beverage or food having an improved flavor according to (17), wherein the S-alkyl(S)-2-methylbutanethioate is S-methyl(S)-2-methylbutanethioate.

Under the above-mentioned situation, the present inventors made an extensive study. As a result, it was found that the above task could be achieved by optically active S-alkyl 2-methylbutanethioates and not by racemic S-alkyl 2-methylbutanethioates used widely in the market. Specifically explaining, it was first found that the flavor composition or fragrance composition comprising an S-alkyl(R)-2-methylbutanethioate as an active ingredient has a flavor or fragrance which is strong and fresh, and reminds a passion fruit, well harmonizes with the flavor component or fragrance component used together, and can impart a beautiful, fresh, highly-taste flavor or fragrance which has been insufficient with known similar compounds derived from natural or processed beverages or foods.

The flavor composition or fragrance composition of the present invention comprising an S-alkyl(R)-2-methylbutanethioate as an active ingredient has a flavor or fragrance which is strong and fresh, and reminds a passion fruit, well harmonizes with the flavor composition or fragrance component used together, and can impart a beautiful, fresh, highly-taste flavor or fragrance which has been insufficient with known similar compounds derived from natural or processed beverages or foods. Therefore, the flavor composition or fragrance composition of the present invention can be used widely in the flavor- or fragrance-added products of the present invention, food materials, food additives, health or sanitary materials, etc.

The present inventors further found that the flavor-improving agent of the present invention comprising an S-alkyl(S)-2-methylbutanethioate as an active ingredient, when added to various beverages or foods such as fruit juice drinks, foods and the like, provides a very clear, highly volatile odor reminding ripe fruits, gives an intensified flavor, can provide a beverage or a food both very superior in flavor and/or fragrance, and therefore can enhance the commercial value of the above beverages or foods. The study was continued and the present invention has been completed.

BEST MODE FOR CARRYING OUT THE INVENTION

The present invention is described in detail below.
In the present invention, racemic S-alkyl 2-methylbutanethioates used widely in the market are not used but optically active S-alkyl 2-methylbutanethioates are used. First, in the flavor composition or fragrance composition of the present invention, S-alkyl(R)-2-methylbutanethiontes are used as an essential component. As specific examples of the S-alkyl(R)-2-methylbutanethioates, there can be mentioned S-methyl ester, S-ethyl ester, S-n-propyl ester, S-isopropyl ester, S-butyl ester, S-2-methylpropyl ester, S-pentyl ester, S-2-methylbutyl ester, S-3-methylbutyl ester, S-hexyl ester, S-cis-3-hexenyl ester, S-heptyl ester and S-octyl ester of (R)-2-methylbutanethioic acid.

The S-alkyl(R)-2-methylbutanethioates may be used as an essential component, in one kind or in two or more kinds. Of these compounds, a compound preferred as the essential component of the flavor composition or fragrance composition of the present invention is S-methyl(R)-2-methylbutanethioate.

The S-alkyl(R)-2-methylbutanethioate used in the present invention may be obtained by extraction from natural product, or by optical resolution of racemic form, or may be obtained by chemical synthesis. However, when the S-alkyl(R)-2-methylbutanethioate is used in a large amount, it is obtained preferably by chemical synthesis.

For chemical synthesis of S-alkyl(R)-2-methylbutanethioate, there can be mentioned, for example, a method of converting (R)-2-methylbutanoic acid (a raw material) into an acid halide and then reacting it with an alkylthiol.

For chemical synthesis of (R)-2-methylbutanoic acid, there can be mentioned, for example, a method described in JP-A-1988-239245, that is, a method of using, as a raw material, tiglic acid [(E)-2-methyl-2-butenoic acid] easily obtainable as a commercial product and subjecting it to asymmetric hydrogenation using, as a catalyst, a ruthenium-optically active phosphine complex having a particular absolute configuration.

The above chemical synthesis method for (R)-2-methylbutanoic acid is described in more detail. Tiglic acid is dissolved in a solvent such as methanol or ethanol; the solution is fed into an autoclave purged with an inert gas; thereto is added a ruthenium-optically active phosphine complex of $\frac{1}{100}$ to $\frac{1}{1,000}$ mole per mole of tiglic acid; and hydrogenation is conducted with stirring, at a hydrogen pressure of 4 to 125 kg/cm$^2$ at a temperature of 5 to 50° C. for 1 to 100 hours.

There may also be used a method of using no hydrogen gas as a hydrogen source, described in JP-A-1991-157346. In this method, there is used, as a hydrogen donor, a large excess of a primary or secondary alcohol. After the reaction, the solvent is distilled off and the residue is subjected to distillation under reduced pressure, whereby intended (R)-2-methylbutanoic acid can be obtained.

Incidentally, as the ruthenium-optically active phosphine complex which can be used, there can be mentioned, for example, the following compounds.

$$Ru_xH_yCl_z[(+)-(R-BINAP)]_2(S)_p \quad (1)$$

{wherein (+)-(R-BINAP) is (+)-2,2'-bis(diphenylphosphino)-1,1'-binaphthyl, (+)-2,2'-bis(di-p-methylphenylphosphino)-1,1'-binaphthyl or the like; S is a tertiary amine; y is 0 or 1; when y is 0, x is 2, Z is 4, and p is 1; when y is 1, x is 1, Z is 1, and p is 0.}

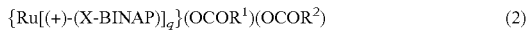

{Ru[(+)-(X-BINAP)]$_q$}(OCOR$^1$)(OCOR$^2$)  (2)

{wherein (+)-(X-BINAP) is (+)-2,2'-bis(diphenylphosphino)-1,1'-binaphthyl wherein the two naphthyl groups may be substituted, at the 5- and 5'-positions, with amino group, acetylamino group or sulfone group and the four phenyl groups may be substituted with lower alkyl group at the p-position; R$^1$ and R$^2$ are each a lower alkyl group, a halogenated lower alkyl group, a phenyl group which may be substituted with lower alkyl group, an α-aminoalkyl group, or an α-aminophenylalkyl group, or, R$^1$ and R$^2$ may be combined together to form an alkylene group; q is 1 or 2.}

{RuH$_l$[(+)-(R-BINAP)]$_v$}Y$_w$  (3)

{wherein (+)-(R-BINAP) is the same as defined above; Y is ClO$_4$, BF$_4$ or PF$_6$; l is 0 or 1; when l is 0, v is 1 and w is 2; when l is 1, v is 2 and w is 1.}

{Ru[(+)-(BIPHEMP)]}Y$_2$  (4)

{wherein (+)-(BIPHEMP) is (+)-2,2'-dimethyl-6,6'-bis(diphenylphosphino)-1,1'-biphenyl, (+)-2,2'-dimethyl-6,6'-bis(di-p-methylphenylphosphino)-1,1'-biphenyl, (+)-2,2'-dimethyl-6,6'-bis(di-p-methoxyphenylphosphino)-1,1'-biphenyl or the like; Y is the same as defined above.}

The above-shown ruthenium-optically active phosphine complexes of (1) to (3) can each be obtained by the method described in JP-A-1988-239245. The ruthenium-optically active phosphine complex of (4) is a complex described in JP-A-1988-145292.

In the flavor composition or fragrance composition of the present invention, the S-alkyl(R)-2-methylbutanethioate obtained as above is preferred to have an optical purity of 50% e.e. ore more.

The S-methyl(R)-2-methylbutanethioate synthesized according to the method described in JP-A-1988-239245 had a high optical purity of about 88% e.e. A test was conducted to examine the optical purity of S-methyl(R)-2-methylbutanethioate at which the (R) isomer began to show its effect. As a result, it was found that the (R) isomer begins to show the effect at an optical purity of about 50% e.e. Based on this result, it was anticipated that the effect of the present invention can be reliably expected also for other thioesters when their optical purities are 50% e.e. or more. Accordingly, it was found that the (R)-thioesters having an optical purity of 50% e.e. or more can be used per se with no purification, as the essential component of the present flavor composition or fragrance composition and can provide various cosmetics, beverages or foods reliably releasing a fragrance or a flavor.

As seen in Examples shown later, the flavor composition or fragrance composition of the present invention containing an S-alkyl(R)-2-methylbutanethioate, for example, as an active ingredient shows a strong, fresh flavor or fragrance which reminds a passion fruit. The S-alkyl(R)-2-methylbutanethioate (which is an active ingredient) exhibits an effect even at a small content and, therefore, can impart a flavor or fragrance to the base materials of various cosmetics, beverages or foods, to be imparted with a flavor or fragrance by a flavor composition or fragrance composition. Meanwhile, racemic S-methyl 2-methylbutanethioate has a natural aroma, but is low in strength, has slight other odors, and has no sufficient effect.

The flavor composition or fragrance composition of the present invention containing an S-alkyl(R)-2-methylbutanethioate, for example, as an active ingredient has, as mentioned above, a widely accepted, superior, strong, fresh flavor or fragrance which reminds a passion fruit and, moreover, has a striking durability and stability for flavor or fragrance. Therefore, by adding the S-alkyl(R)-2-methylbutanethioate, there can be provided a flavor composition or fragrance composition which is accepted widely.

In the flavor composition or fragrance composition of the present invention, there can be used, in addition to the active ingredient with S-alkyl(R)-2-methylbutanethioate or the like, for example, a flavor component and/or a fragrance component ordinarily used. As the other flavor component and/or fragrance component usable, there can be mentioned various synthetic aromachemicals, natural essential oils, synthetic essential oils, citrus oils, animal aromachemicals, etc. Particularly preferred are flower-based or fruit-based flavor components and/or fragrance components; and there can be used, for example, a wide range of flavor components and/or fragrance components, such as described in, for example, Arctander S., "Perfume and Flavor Chemicals", published by the author, Montclair, N.J. (U.S.A), 1969. As representative other components, there can be mentioned α-pinene, limonene, cis-3-hexenol, phenylethyl alcohol, styrallyl acetate, eugenol, rose oxide, linalool, benzaldehyde, muscone, Thesaron (a product of Takasago International Corporation), ethyl butyrate, 2-methylbutanoic acid, etc.

Illustratively, when the S-alkyl(R)-2-methylbutanethioate is added to natural essential oil, for example, bergamot oil, galbanum oil, lemon oil, geranium oil, lavender oil, mandarin oil or the like, there can be prepared a novel flavor composition or fragrance composition having, in addition to the flavor and/or fragrance inherently possessed by the natural essential oil, a flavor and/or fragrance which is mild, deep, fresh and highly-taste and which has durability and holding ability there of are enhanced.

When the S-alkyl(R)-2-methylbutanethioate is added to a flavor composition or fragrance composition such as strawberry, lemon, orange, grapefruit, apple, pineapple, banana, melon, green tea, oolong tea, black tea or the like, which is prepared from various synthetic aromachemicals, natural aromachemicals, natural essential oils, citrus oils, tea extract, animal aromachemicals, etc., there can be prepared a flavor composition or fragrance composition which is imparted with a mild, deep, natural, fruity and tropical odor and further with a fresh and widely accepted odor and which is enhanced in spreadability and durability.

In the flavor composition or fragrance composition of the present invention, the amount of the active ingredient such as S-alkyl(R)-2-methylbutanethioate differs depending upon the kind and use purpose of the flavor composition or fragrance composition; however, in general, the preferred amount is, for example, $10^{-8}$ to $10^9$ ppb, preferably $10^{-7}$ to $10^8$ ppb, more preferably $10^{-6}$ to $10^7$ ppb in the flavor composition, and is, for example, $10^{-8}$ to $10^9$ ppb, preferably $10^{-7}$ to $10^8$ ppb, more preferably $10^{-6}$ to $10^7$ ppb in the fragrance composition.

At least one kind of fixing agent used ordinarily may be added into the flavor composition or fragrance composition of the present invention. There may be used, for example, ethylene glycol, propylene glycol, dipropylene glycol, glycerine, hexylene glycol, benzyl benzoate, triethyl citrate, diethyl phthalate, Hercolyn, medium chain fatty acid triglyceride, and medium chain fatty acid diglyceride.

By adding a flavor composition or fragrance composition containing the S-alkyl(R)-2-methylbutanethioate singly or in combination with the above-mentioned other components, to, for example, a beverage, a food, an oral-care composition, a medicine, a fragrance product, a skin-care preparation, a make-up cosmetic, a hair cosmetic, a sunblock cosmetic, a medicated cosmetic, a hair-care product, a soap, a body cleaner, a bath preparation, a detergent, a fabric softener, a cleaning agent, a kitchen cleaner, a bleaching agent, an aerosol, a deodorant-aromatic, or a sundry, in an appropriate amount capable of imparting the unique flavor and/or fragrance of the S-alkyl(R)-2-methylbutanethioate, there can be provided a product added with a flavor or a product added with a fragrance.

As the product added with a flavor, there can be mentioned, beverages or foods, for example, beverages such as fruit drink, fruit wine, lactic drink, carbonated drink, refreshing drink, other drink and the like; ices such as ice cream, sherbet, ice candy and the like; Japanese-style and Western-style confectionaries; jams; candies; jellies; gums; breads; luxury drinks such as coffee, cocoa, black tea, oolong tea, green tea and the like; soups such as Japanese-style soup, Western-style soup, Chinese-style soup and the like; condiments; instant drinks or foods; snacks; oral-care compositions such as dentifrice, oral cleaner, mouth wash, troche, chewing gum and the like; and medicines such as external preparation for skin (e.g. poultice or ointment), internal medicine and the like.

As the product added with a fragrance, there can be mentioned, for example, the followings.

There can be mentioned, as fragrance product, perfume, eau de parfum, eau de toilette, cologne, etc.; as skin-care preparation, face washing cream, vanishing cream, cleansing cream, cold cream, massage cream, milky lotion, toilet water, liquid foundation, pack, makeup remover, etc; as make-up cosmetic, foundation, face powder, pressed powder, talcum powder, lipstick, rouge, lip cream, cheek rouge, eye liner, mascara, eye shadow, eyebrow pencil, eye pack, nail enamel, enamel remover, etc.; and, as hair cosmetic, pomade, brilliantine, set lotion, hair stick, hair solid, hair oil, hair treatment, hair cream, hair tonic, hair liquid, hair spray, bandlin, hair growth agent, hairdye, etc.

There can be mentioned, as suntan cosmetic, suntan product, sunscreen product, etc.; as medicated cosmetic, antiperspirant, after shave lotion and gel, permanent wave agent, medicated soap, medicated shampoo, medicated skin cosmetic, etc.; as hair-care product, shampoo, rinse, rins-in-shampoo, conditioner, treatment, hair pack, etc.; as soap, toilet soap, bath soap, perfumed soap, transparent soap, synthetic soap, etc.; as body cleaner, body soap, body shampoo, hand soap, etc.; and, as bath preparation, bath preparations (e.g. bath salt, bath tablet and bath liquid), foam bath (e.g. bubble bath), bath oils (e.g. bath perfume and bath capsule), milk bath, bath jelly, bath cube, etc.

There can be mentioned, as detergent, heavy-duty detergent for clothing, light-duty detergent for clothing, liquid detergent, washing soap, compact detergent, soap powder, etc.; as fabric softener, softener, furniture care, etc.; as cleaning agent, cleanser, house cleaner, toilet cleaner, bath cleaner, glass cleaner, mold remover, cleaner for waste pipe, etc.; as cleaner for kitchen, soap for kitchen, synthetic soap for kitchen, cleaner for dishes, etc.; as bleaching agent, oxidation type bleaching agent (e.g. chlorine-based bleaching agent or oxygen-based bleaching agent), reduction type bleaching agent (e.g. sulfur-based bleaching agent), optical bleaching agent, etc.; as aerosol, spray type, powder spray type, etc.; as deodorant-aromatic, solid type, gel type, liquid type, etc.; and, as sundry, tissue paper, toilet paper, etc.

When the flavor composition or fragrance composition of the present invention containing an S-alkyl(R)-2-methylbutanethioate as an essential component is used in a beverage, a food, an oral-care composition, a medicine, a fragrance product, a skin-care preparation, a make-up cosmetic, a hair cosmetic, a sunblock cosmetic, a medicated cosmetic, a hair-care product, a soap, a body cleaner, a bath preparation, a detergent, a fabric softener, a cleaning agent, a kitchen cleaner, a bleaching agent, an aerosol, a deodorant-aromatic, a sundry, etc., the present flavor composition or fragrance composition can be used in any desired form meeting the intended application, selected from the followings. That is, the composition per se; a liquid form obtained by dissolving the composition in, for example, an alcohol or a polyalcohol (e.g. propylene glycol or glycerine); a natural gum (e.g. gum arabic or tragacanth gum) form; an emulsion form obtained by emulsifying the composition with an emulsifier such as glycerine-fatty acid ester, saccharose-fatty acid ester, processed starch or the like; a powder form obtained by coating the composition with an excipient such as natural gum (e.g. arabic gum), gelatin, dextrin or the like; a solution or dispersion form obtained by dissolving or dispersing the composition using a surfactant such as nonionic surfactant, anionic surfactant, cationic surfactant, amphoteric surfactant or the like; a micro-capsule form obtained by treating the composition with a capsuling agent; and so forth.

The flavor composition or fragrance composition can also be used by being included in an inclusion agent (e.g. cyclodextrin) for stability and releasable state. The composition after inclusion is suited for the form of final product, such as liquid, solid, powder, gel, mist, aerosol or the like, and is appropriately selected and used.

The amount of S-methyl(R)-2-methylbutanethioate used in flavor-added product (e.g. beverage, food, oral-care composition or medicine) is appropriately determined depending upon the effect and function expected for each product; however, the amount is generally about $10^{-9}$ to $10^5$ ppb.

The amount of S-alkyl(R)-2-methylbutanethioate used in fragrance-added product (e.g. fragrance product, skin-care preparation, make-up cosmetic, hair cosmetic, sunblock cosmetic, medicated cosmetic, hair-care product, soap, body cleaner, bath preparation, detergent, fabric softener, cleaning agent, kitchen cleaner, bleaching agent, aerosol, deodorant-aromatic or sundry) is appropriately determined depending upon the effect and function expected for each product; however, the amount is generally about $10^{-9}$ to $10^7$ ppb.

Meanwhile, in the flavor-improving agent of the present invention, S-alkyl(S)-2-methylbutanethioates are used as an essential component. As specific examples of the S-alkyl(S)-2-methylbutanethioates, there can be mentioned S-methyl ester, S-ethyl ester, S-n-propyl ester, S-isopropyl ester, S-butyl ester, S-2-methylpropyl ester, S-pentyl ester, S-2-methylbutyl ester, S-3-methylbutyl ester, S-hexyl ester, S-cis-3-hexenyl ester, S-heptyl ester and S-octyl ester of (S)-2-methylbutanethioic acid.

The S-alkyl(S)-2-methylbutanethioates may be used as an essential component in one kind or in two or more kinds. Of these compounds, preferred as the essential component of the flavor-improving agent of the present invention is S-methyl (S)-2-methylbutanethioate.

The S-alkyl(S)-2-methylbutanethioate used in the present invention may be obtained by extraction from natural product, or by chemical synthesis. However, when the S-alkyl(S)-2-methylbutanethioate is used in a large amount, it is preferably obtained by chemical synthesis.

For chemical synthesis of the S-alkyl(S)-2-methylbutanethioate, there can be mentioned, as in the above-mentioned chemical synthesis of S-alkyl(R)-2-methylbutanethioate, for example, a method of converting (S)-2-methylbutanoic acid (a raw material) into an acid halide and then reacting it with an alkylthiol. For chemical synthesis of the (S)-2-methylbutanoic acid, there can be mentioned, for example, a method described in JP-A-1988-239245 or JP-A-1991-157346.

In the flavor-improving agent of the present invention, the S-alkyl(S)-2-methylbutanethioate obtained as above needs to have an optical purity of 70% e.e. or more.

The S-alkyl(S)-2-methylbutanethioate synthesized according to the method described in JP-A-1988-239245 had a high optical purity of about 75% e.e. A test was conducted to examine the optical purity of S-alkyl(S)-2-methylbutanethioate at which the (S) isomer begins to show its effect. As a result, it was found that, in the present invention, the (S) isomer begins to show the effect at an optical purity of about 70% e.e. Accordingly, it was found that the (S)-thioesters having an optical purity of 70% e.e. or more can be used per se with no purification, as the essential component of the present flavor-improving agent and can provide a beverages or a food reliably giving a flavor and releasing an odor.

Here, the release of odor means not only a state in which the flavor of beverage or food spreads in the mouth in a moment, but also a state in which the odor of beverage or food is felt with the mere presence of the beverage or food in the vicinity of the mouth.

In order to obtain an S-alkyl(S)-2-methylbutanethioate having an optical purity of 70% e.e. or more, it is possible to appropriately mix an S-alkyl (S)-2-methylbutanethioate of high optical purity obtained by the above-mentioned synthesis method, with a racemic S-alkyl 2-methylbutanethioate which is known to be widely present in nature, particularly in fruits, beer, etc.

With respect to racemic S-alkyl 2-methylbutanethioates, it is known that, for example, S-methyl 2-methylbutanethioate is present in beer, hop, cheese, etc., S-ethyl 2-methylbutanethioate is present in durian, etc., and S-butyl 2-methylbutanethioate is present in galbanum, etc. It is also known that S-n-propyl ester, S-isopropyl ester, S-butyl ester, S-2-methylpropyl ester, S-pentyl ester, S-2-methylbutyl ester, S-3-methylbutyl ester, S-hexyl ester, S-cis-3-hexenyl ester, S-heptyl ester, S-octyl ester, etc. of 2-methylbutanethioic acid are present in various fruits, etc.

The flavor-improving agent of the present invention contains one or more kinds of the above-obtained S-alkyl(S)-2-methylbutanethioates having an optical purity of 70% e.e. or more and, as necessary, other component (e.g. flavor), and is added to beverages or foods. The other component (e.g. flavor) used in the flavor-improving agent has no particular restriction as long as it is used as an ordinary flavor for foods. The content of the S-alkyl(S)-2-methylbutanethioate in the present flavor-improving agent is not particularly restricted but is preferably about 1 to 15% by weight.

The beverage or food having an improved flavor, of the present invention contains the flavor-improving agent of the present invention which contains one or more kinds of S-alkyl (S)-2-methylbutanethioates having an optical purity of 70% e.e. or more and, as necessary, other component (e.g. flavor), and is improved in flavor and release of odor. The amount of the present flavor-improving agent added to beverage or food can be appropriately varied depending upon the kind of the beverage or food; however, the amount (as S-alkyl(S)-2-methylbutanethioate) in beverage or food is about $10^{-8}$ to $10^5$ ppb (when reduced to optical purity 100%). When the addition amount is small (less than about $10^{-8}$ ppb), no clear effect of addition is seen; and, when the addition amount is large (more than about $10^5$ ppb), the flavor of beverage or food per se may be impaired.

When the flavor-improving agent of the present invention is added to a beverage, in particular, the addition amount to the beverage is preferably about 1 to 100 ppm in terms of S-alkyl (S)-2-methylbutanethioate.

The beverage or food to which the present flavor-improving agent is added, may be any beverage or food as long as flavor improvement is expected by the addition. There can be mentioned, as the food, cakes (e.g. caramel, candy, chocolate, chewing gum and baked sweet), ices (e.g. ice cream and sherbet), pudding, jelly, etc. As the beverage, there can be mentioned carbonated drinks (e.g. cider, lemon lime, fruit soda, guarana and cola), fruit juice drinks free from any fruit juice or containing a natural fruit juice, nectar, concentrated syrup for dilution, lactic drinks, luxury drinks, functional drinks, alcoholic liquors having origins in Western countries (e.g. whisky and wine), etc.

EXAMPLES

The present invention is described in detail below by way of Examples and Comparative Examples. However, the present invention is in no way restricted by them and can be changed as long as there is no deviation from the gist of the present invention.

Incidentally, in the Examples and Comparative Examples, odor was expressed referring to the expression made in "KORYO NO JISSAI CHISHIKI (Practical Knowledge of flavors or fragrances)" (1975, Mar. 25) written by Motoichi Indo, TOYO KEIZAI SHINPOSHA, page 3. Also in the Examples and Comparative Examples, the units of formulations in Tables are parts by weight.

In the analyses in Examples, the following analytical apparatuses were used.

Optical rotation:
DIP-370 (a product of JASCO corporation)
Proton NMR spectrum ($^1$H-NMR):
AM-400 (400 MHz) (a product of Brucker Bio-Spin GmbH)
Tetramethylsilane was used as an internal standard substance.
Infrared absorption spectrum (IR):
Nicolet Avatar 360 FT-IR (a product of Nicolet Japan)
Mass spectrum (MS):
M-80B mass spectrometer (ionization voltage: 20 V) (a product of Hitachi, Ltd.)
Gas chromatography
HP-5890 (a product of Hewlett Packard)
The column used was PEG BC-WAX (0.25 mm×50 mm) (a product of GL. Sciences Inc.).

Synthesis Example 1

Production of (R)-2-methylbutanoic acid 0.2 g (2 mmol) of tiglic acid and 20 ml of methanol were placed in a 100-ml, stainless steel-made autoclave purged with nitrogen. Successively, there was placed 6.0 mg (0.007 mmol) of Ru[(+)-BINAP](BF$_4$)$_2$ {(+)-BINAP is (+)-2,2'-bis (diphenylphosphino)-1,1'-binaphthyl}. Hydrogenation was conducted with stirring, at a hydrogen pressure of 4 kg/cm$^2$ at a reaction temperature of 20° C. for 12 hours. The solvent was distilled off to obtain 0.2 g (yield: 100%) of intended (R)-2-methylbutanoic acid. The optical rotation was $[\alpha]_D^{25}$=−16.7° (neat) and the purity by gas chromatography was 100%. The acid was reacted with (S)-1-phenylethylamine to synthesize an amide; and the amide was analyzed by gas chromatography. As a result, the optical purity of (R)-2-methylbutanoic acid was 88% e.e.

Synthesis Example 2

Production of (R)-2-methylbutanoic acid chloride 50.0 g (420 mmol) of thionyl chloride was dropwise added, at 50° C. in 3 hours, to 35.8 g (350 mmol) of the (R)-2-methylbutanoic acid {$[\alpha]_D^{25}$=−16.7° (neat)} obtained in Synthesis Example 1. Then, a reaction was allowed to take place at 80° C. for 1 hour. Excessive thionyl chloride was distilled off under reduced pressure. The residue was subjected to distillation under reduced pressure to obtain 40.4 g (yield: 96%) of (R)-2-methylbutanoic acid chloride.

Boiling point: 35° C./0.1 torr $^1$H-NMR (CDCl$_3$): 0.98 (t, J=7.5 Hz, 3H), 1.29 (d, J=6.9 Hz, 3H), 1.58~1.66 (m, 1H), 1.79~1.87 (m, 1H), 2.78~2.85 (m, 1H)

$^{13}$C-NMR: 11.46 (CH$_3$), 16.88 (CH$_3$), 26.91 (CH$_2$), 53.29 (CH), 178.05 (CO)

Synthesis Example 3

Production of S-methyl(R)-2-methylbutanethioate 16.1 g (120 mmol) of the (R)-2-methylbutanoic acid chloride obtained in Synthesis Example 2 was dropwise added, in 1 hour with stirring, to a 0° C. mixture of 75 g of a 15% aqueous methylmercaptan solution and 100 ml of diethyl ether. The organic layer was separated and washed with an aqueous sodium chloride solution. The diethyl ether was distilled off. The residue was concentrated under reduced pressure to obtain 15.1 g (yield: 86%) of S-methyl(R)-2-methylbutanethioate. The product was analyzed by gas chromatography. As a result, the chemical purity was 100% and the optical purity was 88% e.e.

Boiling point: 32° C./5 torr $[\alpha]_D^{20}$: −36.7° (neat)

$^1$H-NMR (CDCl$_3$): 0.92 (t, J=7.5 Hz, 3H), 1.29 (d, J=6.9 Hz, 3H), 1.43~1.52 (m, 1H), 1.70~1.78 (m, 1H), 2.28 (s, 3H), 2.54~2.60 (m, 1H)

$^{13}$C-NMR: 11.29 (CH$_3$), 11.58 (CH$_3$), 17.21 (CH$_3$), 27.17 (CH$_2$), 50.04 (CH), 204.22 (CO)

Example 1

Evaluation of Fragrance or Flavor

Each of the S-methyl(R)-2-methylbutanethioates obtained in Synthesis Examples was put on a bottle mouth and filter paper, and sensory evaluation was carried out by perfumers or flavorists having 5 years or more of experience. The evaluation results are shown in Table 1.

TABLE 1

| Compound name | Odor characteristics |
|---|---|
| S-methyl (R)-2-methylbutanethioate | A beautiful, fresh, highly-taste, unique, strong odor which reminds a strong, fresh passion fruit. |
| S-methyl 2-methylbutanethioate (racemic form)* | An odor which is natural but is low in strength and has slight other smells. |

*a product of Oxford Chemicals

As seen above, the S-methyl(R)-2-methylbutanethioate used in the flavor composition or fragrance composition of the present invention had a beautiful, fresh, highly-taste, unique, strong flavor and fragrance which reminded a strong, fresh passion fruit. Meanwhile, all the perfumers or flavorists pointed out that the racemic S-methyl 2-methylbutanethioate had an odor which was natural but was low in strength and had slight other smells.

Example 2

The S-methyl(R)-2-methylbutanethioate synthesized based on the method described in JP-A-1988-239245 had a high optical purity of about 88% e.e. A test was conducted to examine the optical purity of S-methyl(R)-2-methylbutanethioate at which the (R) isomer begins to show its effect reliably. Racemic S-methyl 2-methylbutanethioate was mixed with S-methyl(R)-2-methylbutanethioate in various proportions to prepare (R) dominant compositions of different optical purities. Using these (R) dominant compositions, the optical purity of S-methyl(R)-2-methylbutanethioate at which the effect of the (R) isomer could be clearly felt, was measured by applying a 2:2 point identification test described in 54 page of "Kanno Kensa Nyumon (Introduction to Sensory Test)" (Sato Makoto) published by K.K. Nikka Giren Shuppansha on Oct. 16, 1978. In the method, two kinds of samples A and B are distinguished from each other as follows. That is, the samples A and B are presented to panelers as distinct samples and their characteristics are memorized by the panelers; then, the samples A and B are presented to them as blind samples to allow them to pick up a sample different from the sample A; this operation is repeated a plurality of times; thereby, the difference between the samples is judged based on the number of correct answers obtained.

As a result, it was found that S-methyl(R)-2-methylbutanethioate, when having an optical purity of 50% e.e. or more, can be used per se without being purified, for preparation of a flavor or fragrance composition reliably improved in flavor or fragrance.

Example 3 and Comparative Example 1

The S-methyl(R)-2-methylbutanethioate obtained in the Synthesis Examples was added to a grapefruit flavor composition shown in Table 2, to prepare a flavor composition of Example 3 containing the effective ingredient at a concentration of 0.01 ppb. Racemic S-methyl 2-methylbutanethioate was added to the same grapefruit flavor composition to prepare a flavor composition of Comparative Example 1. The two flavor compositions were subjected to an organoleptic test by flavorists each having an experience of at least 5 years.

TABLE 2

| Component | Example 3 | Comparative Example 1 |
|---|---|---|
| Grape fruit essence | 95.0 | 95.0 |
| Ethyl butanoate | 0.1 | 0.1 |
| Ethyl 2-methylbutanoate | 0.02 | 0.02 |
| Octanal | 0.01 | 0.01 |
| Nootkatone | 0.05 | 0.05 |
| S-methyl (R)-2-methylbutanethioate | 0.000001 | — |
| Racemic S-methyl 2-methylbutanethioate | — | 0.000001 |
| Ethanol | Balance | Balance |
| Total | 100.0 | 100.0 |

As a result, it was pointed out by all the flavorists that the flavor composition of Example 3 was imparted with a natural, deep, fresh flavor not possessed by the flavor composition of Comparative Example 1.

Example 4

Production of Fragrance Composition for Shampoo

Formulation 1
Component

| | |
|---|---:|
| Benzyl salicylate | 55 |
| L-citronellol | 10 |
| Ethyl acetoacetate | 5 |
| Galaxolide 50BB* (a product of IFF) | 390 |
| Geraniol | 10 |
| Hedione (a product of Firmenich S.A.) | 120 |
| Heliobouquet (a product of Takasago International Corporation) | 8 |
| 10% cis-3-hexen-1-ol solution in DPG** | 10 |
| 10% cis-3-hexenyl acetate solution in DPG | 5 |
| Hexylcinnamic aldehyde | 50 |
| β-ionone | 17 |
| Kovanol (a product of Takasago International Corporation) | 40 |
| Lemon oil | 40 |
| Linalool | 45 |
| Linalyl acetate | 45 |
| Nerolidol | 55 |
| Phenylethyl alcohol | 30 |
| Phenylethyl cinnamate | 5 |
| Santalex T (a product of Takasago International Corporation) | 35 |
| 10% Triplal solution in DPG (a product of IFF) | 5 |
| 1% maltol solution in DPG | 15 |
| 10 ppm S-methyl (R)-2-methylbutanethioate solution in DPG | 5 |
| Total | 1000 |

*Benzyl benzoate
**Dipropylene glycol

Comparative Example 2

A fragrance composition for shampoo was prepared in the same formulation as in Example 4 except that, in the formulation of Example 4, the 10 ppm S-methyl(R)-2-methylbutanethioate solution in DPG was replaced by a 10 ppm racemic S-methyl 2-methylbutanethioate solution in DPG.

Application Example 1

Production of Shampoos

The following components including the fragrance composition for shampoo, prepared in Example 4 or Comparative Example 2 were stirred at 80° C. with stirring, until a uniform material were obtained. Then, the uniform material was cooled to 35° C. to prepare a shampoo. The fragrance of each shampoo was evaluated by a sensory test by five perfumers each having an experience of least 5 years.

[Shampoo Composition (Mass %)]

| | |
|---|---:|
| Sodium laurate | 40.00 |
| Disodium N-cocoyl-N-carboxymethylethyl-N-carboxymethylethylenediamime | 10.00 |
| Coconut oil fatty acid diethanolamide (2) | 2.00 |
| Butylene glycol | 2.00 |
| Citric acid | 0.35 |
| Sodium chloride | 0.10 |
| Methylparaben | 0.20 |
| Propylparaben | 0.10 |
| Tetrasodium edetate | 0.10 |
| Fragrance composition of Example 4 or Comparative Example 2 | 0.50 |
| Purified water | Balance |
| Total | 100.00 |

Evaluation Results of Example 4 and Comparative Example 2

The fragrances of the shampoos of Example 4 and Comparative Example 2 were evaluated. As a result, all the perfumers pointed out that the fragrance of the shampoo using the Example 4 formulation containing S-methyl(R)-2-methylbutanethioate was superior in spreadability and gave a fresh and natural feeling.

Example 5

Production of Fragrance Composition for Body Shampoo

Formulation 2
Component

| | |
|---|---:|
| Lemon oil | 100 |
| Lime oil | 180 |
| Geranyl nitrile | 10 |
| 10% aldehyde C-8 solution in DPG | 25 |
| 10% aldehyde C-10 solution in DPG | 35 |
| Ethyl decanoate | 12 |
| Triplal (a product of IFF) | 3 |
| 10% isocyclocitral solution in DPG (a product of IFF) | 25 |
| Styrallyl acetate | 20 |
| α-terpineol | 30 |
| Linalool | 70 |
| Linalyl acetate | 50 |
| Geraniol | 60 |
| Geranyl acetate | 5 |
| Lilial (a product of Givaudan S.A.) | 80 |
| Hexyl cinnamic aldehyde | 120 |
| Myrac aldehyde (a product of IFF) | 15 |
| Cis-3-hexenyl salicylate | 15 |
| β-ionone | 25 |
| Heliotropin | 5 |
| Tonalide (a product of PFW) | 30 |
| Dipropylene glycol | Balance |
| 10 ppm S-methyl (R)-2-methylbutanethioate solution in DPG | 5 |
| Total | 1000 |

Comparative Example 3

A fragrance composition for body shampoo was prepared in the same formulation as in Example 5 except that, in the formulation of Example 5, the 10 ppm S-methyl(R)-2-methylbutanethioate solution in DPG was replaced by a 10 ppm racemic S-methyl 2-methylbutanethioate solution in DPG.

Application Example 2

Production of Body Shampoos

Body shampoos were prepared using the fragrance compositions for body shampoo, prepared in Example 5 and Comparative Example 3. The fragrance of each body shampoo was evaluated by a sensory test by five perfumers each having an experience of least 5 years.

[Body Shampoo Formulation (Mass %)]

| | |
|---|---|
| Dibutylhydroxytoluene | 0.05 |
| Methylparaben | 0.10 |
| Propylparaben | 0.10 |
| Tetrasodium edetate | 0.10 |
| Potassium chloride | 0.20 |
| Glycerine | 5.00 |
| Coconut oil fatty acid diethanolamide (2) | 3.00 |
| Sodium polyoxyethylene lauryl ether acetate (3E.O.) (30%) | 10.00 |
| Coconut oil fatty acid amide propyl betaine solution (34%) | 25.00 |
| Potassium myristate (40%) | 25.00 |
| Fragrance composition of Example 5 or Comparative Example 3 | 0.50 |
| Purified water | Balance |
| Total | 100.00 |

Evaluation Results of Example 5 and Comparative Example 3

The fragrances of the body shampoos of Example 5 and Comparative Example 3 were evaluated. As a result, all the perfumers pointed out that the fragrance of the body shampoo using the Example 5 formulation containing S-methyl(R)-2-methylbutanethioate gave an improved freshness and a citrus feeling.

Example 6

Production of Rosy Fragrance Composition

Formulation 3
Component

| | |
|---|---|
| α-pinene | 8 |
| Aldehyde C-16 | 1 |
| Allyl amyl glycolate | 1 |
| Ambrettolide(a product of IFF) | 8 |
| Bergamot | 15 |
| Carbitol | 100 |
| Cardamon oil | 3 |
| L-citronellol | 30 |
| β-Damascone | 2 |
| 10% dimethyloctanol solution in DPG | 4 |
| Dipropylene glycol | 29 |
| 10% Dynascone solution in DPG | 5 |
| 10% ethyl acetate solution in DPG | 4 |
| Ethyl acetoacetate | 15 |
| 10% galbanum oil solution in DPG | 10 |
| Hedione(a product of Firmenich S.A.) | 195 |
| Heliobouquet (a product of Takasago International Corporation) | 10 |
| Cis-3-hexen-1-ol | 2 |
| 10% cis-3-hexen-1-ol solution in DPG | 3 |
| β-ionone | 10 |
| Jasmine absolute | 3 |
| 10% lime oil solution in DPG | 5 |
| Linalyl acetate | 40 |
| 10% 8-mercaptomenthone solution in DPG | 8 |
| Musk T (a product of Takasago International Corporation) | 200 |
| Nerolidol | 46 |
| Phenylethyl alcohol | 17 |
| β-pinene | 117 |
| Rhubofix(a product of Firmenich S.A.) | 12 |
| Rose absolute | 3 |
| 10% rose oil solution in DPG | 5 |
| 10% L-rose oxide solution in DPG | 15 |

-continued

| | |
|---|---|
| Santalex T (a product of Takasago International Corporation) | 40 |
| Triplal (a product of IFF) | 14 |
| Veloutone(a product of Firmenich S.A.) | 12 |
| Maltol | 5 |
| 10 ppm S-methyl (R)-2-methylbutanethioate solution in DPG | 5 |
| Total | 1000 |

Comparative Example 4

A rosy fragrance composition was prepared in the same formulation as in Example 6 except that, in the formulation of Example 6, the 10 ppm S-methyl(R)-2-methylbutanethioate solution in DPG was replaced by a 10 ppm racemic S-methyl 2-methylbutanethioate solution in DPG.

Application Example 3

Production of Cosmetic Creams

Cosmetic creams were prepared using the rosy fragrance compositions prepared in Example 6 and Comparative Example 4. The fragrance of each cosmetic cream was evaluated by a sensory test by five perfumers each having an experience of least 5 years.

[Cosmetic Cream (Mass %)]

| | |
|---|---|
| Stearyl alcohol | 6.0 |
| Stearic acid | 2.0 |
| Hydrogenated lanolin | 4.0 |
| Squalane | 9.0 |
| Octyl decanol | 10.0 |
| Glycerine | 6.0 |
| Polyethylene glycol 1500 | 4.0 |
| Polyoxyethylene (25) cetyl ether | 3.0 |
| Glycerine monostearate | 2.0 |
| Methylparaben | Appropriate amount |
| Ethylparaben | Appropriate amount |
| Fragrance composition of Example 6 or Comparative Example 4 | 0.1 |
| Purified water | Balance |
| Total | 100.0 |

Evaluation Results of Example 6 and Comparative Example 4

The fragrances of the cosmetic creams of Example 6 and Comparative Example 4 were evaluated. As a result, all the perfumers pointed out that the odor the cosmetic cream using the Example 6 formulation containing S-methyl(R)-2-methylbutanethioate had high spreadability and gave a natural feeling.

Flavors of beverages containing S-methyl(S)-2-methylbutanethioate (namely, the flavor-improving agents of the present invention), and racemic forms thereof (namely, conventional flavors) were compared with each other.

(1) Selection of Panelers

In the same manner as in Example 1 were selected total 10 expert flavorists (8 males and 2 females) of twenties to thirties.

(2) Preparation of Flavor-Improving Agent for Beverage, by Recombination of Formulation A racemic S-alkyl 2-methylbutanethioate in a conventional flavor formulation was replaced by a corresponding (S) isomer to prepare a flavor-improving agent for beverage.

(3) Addition to Beverage

The flavor-improving agent prepared in the above (2) was added to a model beverage; and the flavors when the (S) isomer and the racemate were added, were compared with each other.

Synthetic Example 4

Production of (S)-2-methylbutanoic acid 0.2 g (2 mmol) of tiglic acid and 20 ml of methanol were placed in a 100-ml, stainless steel-made autoclave purged with nitrogen. Successively, there was placed 6.0 mg (0.007 mmol) of Ru[(−)-BINAP](BF$_4$)$_2$ {(−)-BINAP is (−)-2,2'-bis (diphenylphosphino)-1,1'-binaphthyl}. Hydrogenation was conducted with stirring, at a hydrogen pressure of 4 kg/cm$^2$ at a reaction temperature of 20° C. for 12 hours. The solvent was distilled off to obtain 0.2 g (yield: 100%) of intended (S)-2-methylbutanoic acid. The optical rotation was $[\alpha]_D^{25}$=+16.7° (neat) and the purity by gas chromatography was 100%. The acid was reacted with (R)-1-phenylethylamine to synthesize an amide; and the amide was analyzed by gas chromatography. As a result, the optical purity of (S)-(+)-2-methylbutanoic acid was 88% e.e.

Synthesis Example 5

Production of (S)-2-methylbutanoic acid chloride 50.0 g (420 mmol) of thionyl chloride was dropwise added, at 50° C. in 3 hours, to 35.8 g (350 mmol) of the (S)-2-methylbutanoic acid {$[\alpha]_D^{25}$=+16.7° (neat)} obtained in Synthetic Example 4. Then, a reaction was allowed to take place at 80° C. for 1 hour. Excessive thionyl chloride was distilled off under reduced pressure. The residue was subjected to distillation under reduced pressure to obtain 40.4 g (yield: 96%) of (S)-2-methylbutanoic acid chloride.

Boiling point: 35° C./0.1 torr
$^1$H-NMR (CDCl$_3$): 0.98 (t, J=7.5 Hz, 3H), 1.29 (d, J=6.9 Hz, 3H), 1.58~1.66 (m, 1H), 1.79~1.87 (m, 1H), 2.78~2.85 (m, 1H)
$^{13}$C-NMR: 11.46 (CH$_3$), 16.88 (CH$_3$), 26.91 (CH$_2$), 53.29 (CH), 178.05 (CO)

Synthesis Example 6

Production of S-methyl(S)-2-methylbutanethioate 16.1 g (120 mmol) of the (S)-2-methylbutanoic acid chloride obtained in Synthesis Example 5 was dropwise added, in 1 hour with stirring, to a 0° C. mixture of 75 g of a 15% aqueous methylmercaptan solution and 100 ml of diethyl ether. The organic layer was separated and washed with an aqueous sodium chloride solution. The diethyl ether was distilled off. The residue was concentrated under reduced pressure to obtain 15.1 g (yield: 86%) of S-methyl(S)-2-methylbutanethioate. The product was analyzed by gas chromatography. As a result, the chemical purity was 100% and the optical purity was 88% e.e.

Boiling point: 32° C./5 torr
$[\alpha]_D^{20}$: +36.7° (neat)
$^1$H-NMR (CDCl$_3$): 0.92 (t, J=7.5 Hz, 3H), 1.29 (d, J=6.9 Hz, 3H), 1.43~1.52 (m, 1H), 1.70~1.78 (m, 1H), 2.28 (s, 3H), 2.54~2.60 (m, 1H)
$^{13}$C-NMR: 11.29 (CH$_3$), 11.58 (CH$_3$), 17.21 (CH$_3$), 27.17 (CH$_2$), 50.04 (CH), 204.22 (CO)

Example 7 and Comparative Example 5

Evaluation of Flavor

Each of the S-methyl(S)-2-methylbutanethioate obtained in Synthesis Examples was put on a bottle mouth and filter paper, and sensory evaluation was carried out by the above-mentioned panelists. The evaluation results are shown in Table 3.

TABLE 3

| Compound name | Odor Characteristics |
| --- | --- |
| S-methyl (S)-2-methylbutanethioate | A odor which reminds the fruity-note having slight fresh-leafy. And a very clear, spreading odor which is similar to the full ripeness of fruit. |
| S-methyl 2-methylbutanethioate (racemic form)* | An odor which is natural but is low in strength and has slight other smells. |

*a product of Oxford Chemicals

As seen above, the S-methyl(S)-2-methylbutanethioate used in the flavor-improving agent of the present invention had a odor which reminds the fruity-note having slight fresh-leafy. And a very clear, spreading odor which is similar to the full ripeness of fruit. Meanwhile, the racemic form had a odor which was natural but was low in strength and had slight other smells.

Example 8 and Comparative Example 6

Flavor-improving agents for beverage were prepared based on the strawberry flavor formulations shown in Table 4. The flavor-improving agent of Example 8 used the formulation containing the S-methyl(S)-2-methylbutanethioate obtained in Synthesis Example 6, and the flavor-improving agent of Comparative Example 6 used the formulation containing racemic S-methyl 2-methylbutanethioate. These flavor-improving agents for beverage were each added to a fruit juice-free carbonated drink containing 10% by weight of glucose and 0.1% by weight of citric acid, in an amount of 0.1% by weight. Each of the resultant drinks was evaluated for odor by the above-mentioned panelers. The results are shown in Table 5.

TABLE 4

| Component | Example 8 | Comparative Example 6 |
| --- | --- | --- |
| S-methyl (S)-2-methylbutanethioate | 2.000 | — |
| S-methyl 2-methylbutanethioate (racemic form) | — | 2.000 |
| Ethyl butyrate | 1.200 | 1.200 |
| Isoamyl butyrate | 0.140 | 0.140 |
| Butyric acid | 0.900 | 0.900 |
| Ethyl lactate | 0.040 | 0.040 |
| Benzyl alcohol | 2.000 | 2.000 |
| Cis-3-hexenol | 1.000 | 1.000 |
| Linalool | 0.100 | 0.100 |
| Ethyl methylphenylglicidate | 0.120 | 0.120 |
| Hexanal | 0.080 | 0.080 |
| 3-Ethoxy-2-methyl-4-pyrone | 1.500 | 1.500 |

TABLE 4-continued

| Component | Example 8 | Comparative Example 6 |
|---|---|---|
| γ-decalactone | 0.170 | 0.170 |
| γ-undecalactone | 0.140 | 0.140 |
| Ethyl alcohol (95%) | 55.610 | 55.610 |
| Propylene glycol | Balance | Balance |
|  | 100.000 | 100.000 |

TABLE 5

| Sample | Odor | Evaluation of release of odor |
|---|---|---|
| A drink to which the flavor-improving agent of Example 8 containing S-methyl (S)-2-methyl butanethioate was added | A very clear, spreading odor which is similar to the full ripeness of fruit. | 10 persons |
| A drink to which the flavor-improving agent of Comparative Example 6 containing S-methyl 2-methylbutanethioate (racemic form) was added | No clear odor which is similar to the full ripeness of fruit and which is felt when the (S) isomer has been added. | 0 person |

* Evaluation of release of odor indicates the number of persons who gave evaluation of "superior to other sample".

As seen in Table 5, the drink to which the flavor-improving agent for beverage, of Example 8 containing S-methyl(S)-2-methylbutanethioate was added, had a very clear, spreading odor which was similar to the full ripeness of fruit. Meanwhile, the drink to which the flavor-improving agent for beverage, of Comparative Example 6 containing S-methyl 2-methylbutanethioate (racemic form) was added, gave no freshness felt in addition of S-methyl(S)-2-methylbutanethioate.

Example 9

The S-methyl(S)-2-methylbutanethioate synthesized based on the method described in JP-A-1988-239245 had a high optical purity of about 88% e.e. A test was conducted to examine the optical purity of S-methyl(S)-2-methylbutanethioate at which the (S) isomer begins to show its effect reliably. Racemic S-methyl 2-methylbutanethioate was mixed with S-methyl(S)-2-methylbutanethioate in various proportions to prepare (S) dominant compositions of different optical purities. Using these (S) dominant compositions, the optical purity of S-methyl(S)-2-methylbutanethioate at which the effect of the (S) isomer could be clearly felt, was measured by applying a 2:2 point identification method described in 54 page of "Kanno Kensa Nyumon (Introduction to sensory Test)" (Sato Makoto) published by K.K. Nikka Giren Shuppansha on Oct. 16, 1978. In the method, two kinds of samples A and B are distinguished from each other as follows. That is, the samples A and B are presented to panelers as distinct samples and their characteristics are memorized by the panelers; then, the samples A and B are presented to them as blind samples to allow them to pick up a sample different from the sample A; this operation is repeated a plurality of times; thereby, the difference between the samples is judged based on the number of correct answers obtained.

As a result, it was found that S-methyl(S)-2-methylbutanethioate, when having an optical purity of 70% e.e. or more, can be used per se without being purified, for the reliable improvement of the flavor of beverage or food.

The invention claimed is:

1. A flavor composition comprising an S-alkyl (R)-2-methylbutanethioate at a concentration of $10^{-6}$ to $10^7$ ppb.

2. A flavor composition according to claim 1, wherein the S-alkyl (R)-2-methylbutanethioate has an optical purity of 50% e.e. or more.

3. A fragrance composition characterized by comprising an S-alkyl (R)-2-methylbutanethioate at a concentration of $10^{-6}$ to $10^7$ ppb.

4. A flavor-added product comprising a base product and the flavor composition set forth in claim 1.

5. The flavor-added product according to claim 4, which is selected from the group consisting of beverages, foods, oral-care compositions and medicines.

6. A flavor-added product comprising a base product and S-alkyl (R)-2-methylbutanethioate added to the base product at a concentration of $10^{-9}$ to $10^5$ ppb.

7. A fragrance-added product comprising a base product and the fragrance composition set forth in claim 3.

8. The fragrance-added product according to claim 7, which is selected from the group consisting of fragrance products, skin-care preparations, make-up cosmetics, hair cosmetics, sunblock cosmetics, medicated cosmetics, hair-care products, soaps, body cleaners, bath preparations, detergents, fabric softeners, cleaning agents, kitchen cleaners, bleaching agents, aerosols, deodorant-aromatics, repellants and sundries.

9. A fragrance-added product comprising a base product and S-alkyl (R)-2-methylbutanethioate added to the base product at a concentration of $10^{-9}$ to $10^7$ ppb.

* * * * *